United States Patent
Harari et al.

(10) Patent No.: US 7,508,967 B2
(45) Date of Patent: Mar. 24, 2009

(54) RADIATION TREATMENT PLANNING USING CONFORMAL AVOIDANCE

(75) Inventors: Paul M. Harari, Madison, WI (US); Wolfgang A. Tome, Madison, WI (US); Shiyu Song, Richmond, VA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 556 days.

(21) Appl. No.: 11/110,461

(22) Filed: Apr. 20, 2005

(65) Prior Publication Data

US 2006/0083349 A1      Apr. 20, 2006

Related U.S. Application Data

(60) Provisional application No. 60/618,846, filed on Oct. 14, 2004.

(51) Int. Cl.
  *G06K 9/00*   (2006.01)
  *A61N 5/10*   (2006.01)
(52) U.S. Cl. .......................................... 382/128; 378/65
(58) Field of Classification Search .................. 382/65, 382/131, 128, 132; 378/65; 600/1
  See application file for complete search history.

(56) References Cited

U.S. PATENT DOCUMENTS

| | | | |
|---|---|---|---|
| 5,724,400 A * | 3/1998 | Swerdloff et al. | 378/65 |
| 6,152,599 A * | 11/2000 | Salter, Jr. | 378/209 |
| 6,504,899 B2 * | 1/2003 | Pugachev et al. | 378/65 |
| 6,546,073 B1 * | 4/2003 | Lee | 378/65 |
| 6,697,452 B2 * | 2/2004 | Xing | 378/69 |
| 6,704,440 B1 * | 3/2004 | Kump | 382/132 |
| 2002/0080912 A1 * | 6/2002 | Mackie et al. | 378/21 |
| 2002/0080915 A1 * | 6/2002 | Frohlich | 378/65 |
| 2002/0193685 A1 * | 12/2002 | Mate et al. | 600/424 |
| 2003/0191384 A1 * | 10/2003 | Svatos et al. | 600/410 |
| 2003/0212325 A1 * | 11/2003 | Cotrutz et al. | 600/436 |
| 2004/0073107 A1 * | 4/2004 | Sioshansi et al. | 600/431 |
| 2004/0254773 A1 * | 12/2004 | Zhang et al. | 703/11 |

FOREIGN PATENT DOCUMENTS

WO   WO 9817349 A1 *   4/1998
WO   WO 2005057463 A1 *   6/2005

OTHER PUBLICATIONS

Mackie, Thomas Rockwell et al., "Image Guidance For Precise Conformal Radiotherapy." Elsevier Inc., Int. J. Radiation Oncology Biol. Phys., Apr. 8, 2003, vol. 56, No. 1, pp. 89-105.*

(Continued)

*Primary Examiner*—Andrew W Johns
(74) *Attorney, Agent, or Firm*—Boyle Fredrickson, S.C.

(57) ABSTRACT

A system and method of radiation planning. The system and method are configured to implement or include the steps of (a) obtaining an image of a patient encompassing tumorous and non-tumorous tissue, (b) applying an encompassing field to the image having an area covering the tumorous and non-tumorous tissue, (c) using a graphical user interface to subtract subset fields from the encompassing field corresponding to radiation sensitive non-tumorous tissues to define a treatment area, and (d) inputting the treatment area to a computer program to generate a radiation treatment plan based on at least one prescribed dose to the treatment area.

21 Claims, 3 Drawing Sheets

OTHER PUBLICATIONS

Mackie, Rock, "IMRT", International Workshop In IMRT 2002, pp. 1-16, slides 1-95.*

Tome, Wolfgang et al., "Optically guided intensity modulated radiotherapy" Elsevier Inc., Radiotherapy and Oncology, vol. 61, Issue 1, Oct. 2001, pp. 33-44.*

Aldridge, Jennifer Stacy, Tomographic Patient Registration & Conformal Avoidance Tomotherapy, UMI Microform 9956235, 1999, Bell & Howell Information and Learning Company, Ann Arbor Michigan.

* cited by examiner

RADIATION TREATMENT PLANNING USING CONFORMAL AVOIDANCE

CROSS-REFERENCE TO RELATED APPLICATIONS

This application is based on provisional application Ser. No. 60/618,846 filed Oct. 14, 2004 and entitled Radiation Treatment Planning Using Conformal Avoidance.

STATEMENT REGARDING FEDERALLY SPONSORED RESEARCH OR DEVELOPMENT

This invention was made with United States government support awarded by the following agencies; NIH CA88960. The United States has certain rights in this invention.

BACKGROUND OF THE INVENTION

The present invention relates generally to radiation therapy planning for the treatment of tumors, and in particular, radiation treatment planning for radiation therapy machines that provide independent intensity modulation of many narrow beams of radiation.

External beam radiation therapy involves the treatment of tumorous tissue with high-energy radiation according to a treatment plan. The treatment plan controls the radiation's placement and intensity, and thus the dose level to volume elements of tissue within a treatment volume so that the tumorous tissue within the treatment volume receives a sufficient dose of radiation while radiation to the surrounding and adjacent non-tumorous tissue is minimized.

Intensity modulated radiation therapy (IMRT) treats a patient with multiple smaller rays of radiation, each substantially smaller than the treatment volume and independently controllable in intensity and/or energy. The rays are directed at different angles at the patient and combined to produce the desired dose pattern. Typically, the radiation source consists of either high energy x-rays, electrons from certain linear accelerators, or gamma rays from highly focused radioisotopes such as $Co^{60}$.

Radiation plays a central role in the treatment of head and neck (H&N) cancer patients. Conventional H&N radiation treatment is associated with substantial toxicity to normal tissue, and IMRT provides the opportunity to deliver radiation in H&N with enhanced conformance to tumor targets while diminishing the radiation dose to the surrounding normal tissue structures. Unfortunately, tumor target definition in H&N cancer is complex and the delivery of IMRT requires accurate and thorough target definition. Experienced H&N cancer specialists commonly consume several hours to fully contour and refine desired targets for a single H&N IMRT case. A substantial part of the complexity arises from the need to define not only the gross tumor volume (GTV) containing the tumor, but also to describe a contour containing surrounding lymph nodes. The lymph nodes can be very difficult to image and thus to distinguish from other tissue.

The complexity of the planning process associated with IMRT, a particularly in H&N IMRT may discourage the use of highly effect IMRT techniques.

SUMMARY OF THE INVENTION

The present invention provides a radiation treatment planning method which reverses the process normally used for treatment planning from that of describing the tumor volume and in some cases the surrounding lymph node areas, to one of describing areas of normal tissue and subtracting those areas from an encompassing field covering both normal and tumorous tissue types. Normal tissue structure in H&N treatment such as salivary glands and the spinal cord are more clearly defined in image studies and therefore easier to contour reproducibly than less well defined elective nodal or "at risk regions". Physician planning time, using this method, can be reduced by as much as three times, and preliminary analysis in H&N planning shows that salivary gland and spinal cord protection is equivalent to that achieved with a conventional "target definition" approach. The method of the present invention may also have application outside of the head and neck area.

Specifically then, the present invention provides a method of radiation planning comprising steps of obtaining an image of the patient encompassing tumorous and non-tumorous tissue and applying an encompassing field to the image having an area covering the tumorous and non-tumorous tissue. A graphical user interface is used by a physician to define a subset field of normal tissue for subtraction from the encompassing field. The resulting treatment area may then be input to a computer program (being separate or the same as that providing for the graphical user interface) to generate a radiation treatment plan using at least one prescribed dose to the treatment area.

It is thus one object of at least one embodiment of the invention to improve the acceptance of IMRT in head and neck cancer treatment or any treatment where complex treatment areas must be created by simplifying treatment planning.

It is another object of at least one embodiment of the invention to allow treatment area definition based on the more easily identified structure of normal tissue rather than the often more difficult to identify tumor tissues and surrounding elective areas.

The method may include the step of using the graphical user interface to subdivide the treatment area into at least two zones and applying different prescribed doses to the zones.

Thus it is another object of at least one embodiment of the invention to allow rapid treatment planning while allowing a set of different doses within the treatment area.

The encompassing field may be a slice through the head and neck region defined by the exposure area of two counter-directed beams from the particular radiation therapy equipment, the beams extending along a lateral access through the head and neck region.

Thus it is one object of at least one embodiment of the invention to provide an extremely simple definition of the encompassing field for H&N treatment using a beam configuration familiar to H&N.

The image may be a medial slice through the head and neck region and the subset fields may be selected from the group covering a spinal cord, parotid gland, mandible, and area outside the mandible.

Thus it is another object of at least one embodiment of the invention to use subset fields matched to readily identifiable anatomical structures.

The encompassing field may be applied to the image by tracing a periphery of the desired encompassing field. This tracing may be done manually or by automatic techniques following, for example, an isodose line of the unmodulated beams.

Thus it is another object of at least one embodiment of the invention to provide a simple method of rapidly defining an encompassing field.

Alternatively, the encompassing field may be a predefined pattern from a library of encompassing fields for different procedures and the step of applying the encompassing field may be the step of fitting one encompassing field from the library to the patient image based on anatomical landmarks. For example, the fitting may be a translation and rotation of the selected encompassing field or a warping of the selected encompassing field. A similar procedure may be adopted for defining the subset fields.

Thus it is another object of at least one embodiment of the invention to provide a rapid method of creating treatment plans by reusing general encompassing fields and/or subset fields that will fit a wide variety of patients with simple modification.

These particular objects and advantages may apply to only some embodiments falling within the claims and thus do not define the scope of the invention.

DETAILED DESCRIPTION OF THE PREFERRED EMBODIMENT

Figure 1:
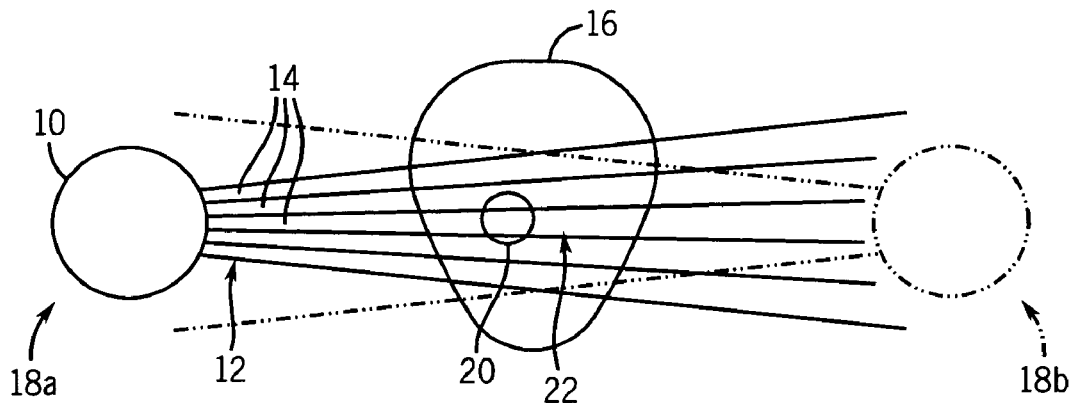
FIG. 1 is a simplified diagram of a transverse cross-section of the head and neck region showing the position of laterally opposed IMRT radiation sources whose unmodulated beams describe an encompassing area.

Referring now to FIG. 1, a radiation source for an IMRT radiation therapy system provides a beam 12 comprised of multiple rays 14 each of which may be independently modulated as to intensity and/or energy according to methods well known in the art.

For head and neck radiation therapy, the radiation source 10 may be positioned alternately on left and right lateral sides of a patient's head and neck 16 at lateral positions 18a and 18b opposed about the head and neck 16 to irradiate a tumor volume 20 and the region 22 surrounding the tumor.

Figure 2:
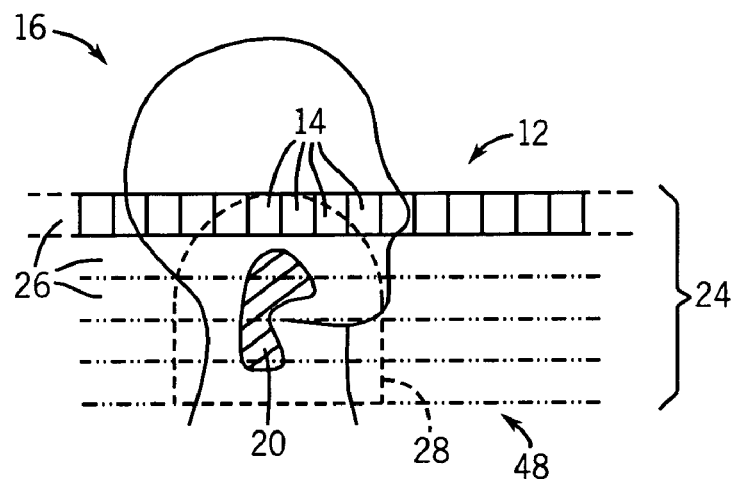
FIG. 2 is a lateral view of the head and neck region of FIG. 1 showing a series of treatment planes that may be obtained by movement of the IMRT beams of FIG. 1 vertically and showing preliminary beam collimation describing the modulated areas of the beams of FIG. 1 and a tumor outline.

Referring also to FIG. 2, the radiation beam 12 from the lateral positions 18a and 18b may expose a single transverse slice 26 of the patient, and the entire vertical height of the treatment area 24 may be covered by a series of successive vertically repositionings of the source 10 at each of lateral positions 18a and 18b.

Figure 3:
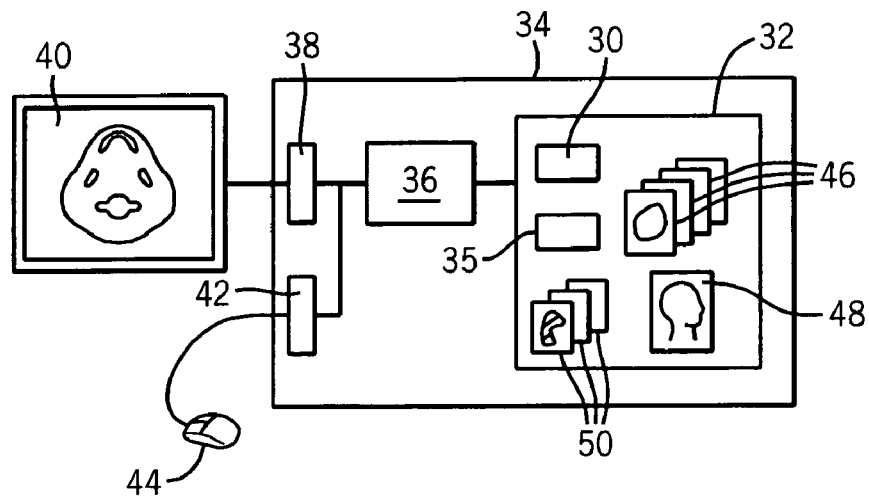
FIG. 3 is a block diagram of a standard electronic computer that may store images of the patient per FIGS. 1 and 2 and may execute a stored program in accordance with the present invention.

Referring now to FIG. 3, the present invention generally provides a target definition program 30 that may define a dose map providing a desired dose distribution in each of the slices 26. The target definition program 30 may be stored in the memory 32 of an electronic computer 34 and executed by a processor 36. The electronic computer 34 includes interfaces 38 and 42 allowing it to communicate with a graphic monitor 40 and cursor control device 44 such as a mouse or track ball, light pen or other device well known in the art.

The memory 32 may also hold a series of CT slice images 46 taken of the patient along each of the slices 26 per FIG. 2 as will be understood in the art using a conventional CT machine. Optionally, the memory 32 may also include a treatment planning program 35, also of the type well known in the art, that takes the dose map produced by the target definition program 30 for each of the slices 26 to calculate the necessary intensities and sequences of the rays 14 of the beams 12 for a particular radiation therapy machine. The memory 32 may also include a template library 50 holding subset areas as will be described below.

Figure 4:
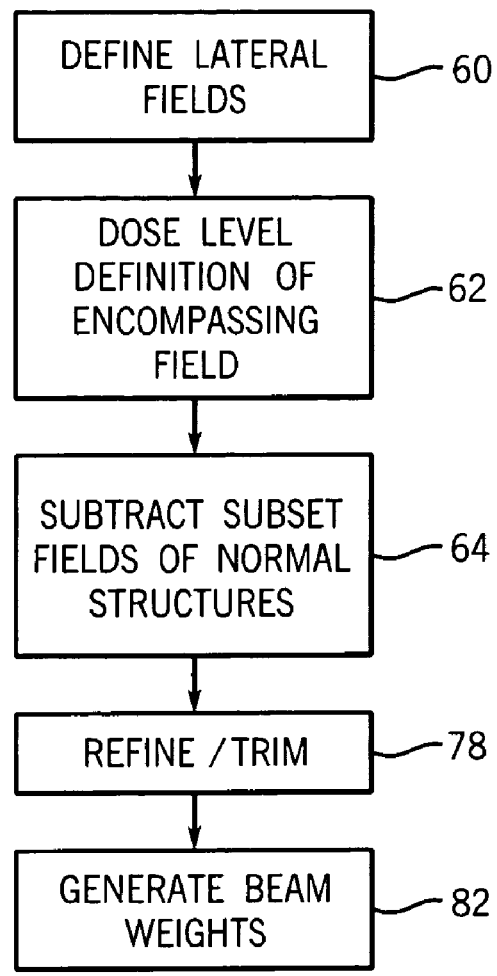
FIG. 4 is a flow chart of the steps of the present invention as may be executed using the computer of FIG. 3 executing the stored program.

Referring now to FIGS. 2 and 4, in a first step of the target definition program 30 as indicated by process block 60, the tumor volume 20 and a lateral field 28 (shown in FIG. 2) are defined.

Generally, the tumor volume may be identified by tracing on each CT slice image 46 a boundary surrounding the tumor. The tracings for each slice are then joined into the tumor volume 20 by interpolation between slices.

The lateral field 28 describes for each of the slices 26, a collimated anterior-posterior width of the beam 12. The beam width is set to amply cover the tumor volume 20 and a margin of tissue around the tumor volume 20 sufficient to cover any elective treatment area. So long as the lateral field 28 is reasonably generous, it need not be precisely set because actual dose within the lateral field 28 will be further controlled by the modulation of the radiation beams.

The lateral field 28 is most easily defined by creating a lateral image 48 (shown in FIG. 3) of the orientation of FIG. 2 showing the tumor volume 20, and using the lateral image 48 as a basis for tracing the lateral field 28 on the lateral image 48. The lateral image 48 may, for example, be generated from the CT images 46 (shown in FIG. 3) by a simple rebinning of the data.

Figure 5:
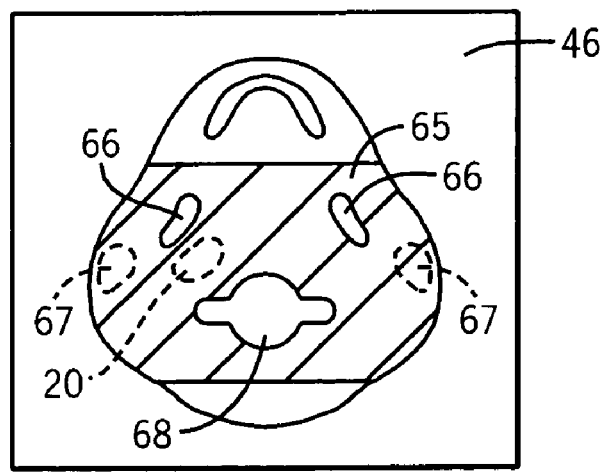
FIG. 5 is a transverse image slice of the patient of FIGS. 1 and 2 showing an encompassing field derived by a tracing of the 85% isodose line of the collimated beams of FIG. 2.

Referring now to FIGS. 4 and 5 at succeeding process block 62 for each of the CT images 46, an encompassing field 65 may be defined and displayed superimposed on the CT slice image 46. The encompassing field 65 may, for example, be defined as the 85% isodose line from the source 10 positioned at positions 18a and 18b collimated to produce the lateral fields 28 but otherwise unmodulated.

As will be seen from FIG. 5, the encompassing field 65 in the case of H&N treatment will generally be a horizontal band extending laterally across the transverse CT slice image 46 from a point posterior to the back of the mandible 66 to a point anterior to the spinal column 68. This encompassing field 65 will thus cover the tumor volume 20 as well as nodal areas or at risk areas surrounding the tumor volume 20 which can be extremely difficult to define and outline.

Other methods of defining the encompassing field 65 may be used including a simple tracing or painting process well known to those in the graphical imaging art or application of a library of pre-defined fields from a library as will be described below.

Figure 6:
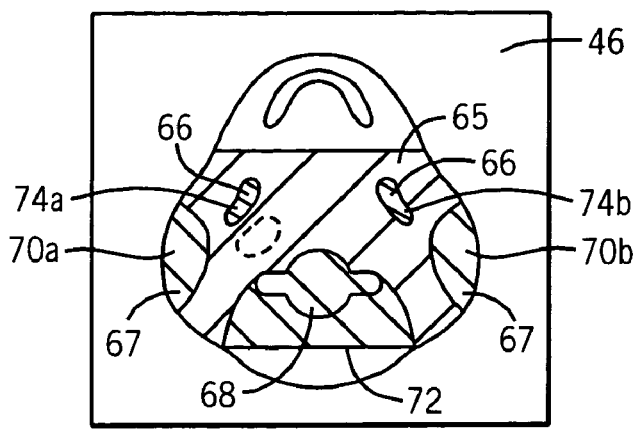
FIG. 6 is a figure similar to that of FIG. 5 showing the application of subset fields to the encompassing field of FIG. 5 over the mandible, salivary glands, and spinal cord.

Referring now to FIGS. 4 and 6 at succeeding process block 64, subset fields may be subtracted from the encompassing field 65. These subset fields, in this example, will include subset fields 70a and 70b covering the salivary glands 67, subset field 72 covering the spinal column 68, and subset fields 74a and 74b covering the mandible. As mentioned before, these normal tissue structures covered by the subset fields 70, 72, and 74 are relatively easy to identify in the CT slice images 46 and may be quickly outlined through the use of the cursor control device 44 by a physician.

Alternatively, a standard library subset field may be used and library subset fields fit to the anatomical structures of the CT slice images 46 as will be described below.

Figure 7:
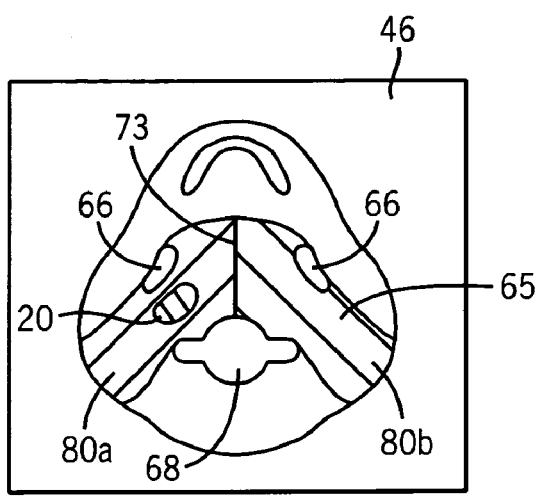
FIG. 7 is a figure similar to that of FIG. 6 showing trimming of the encompassing area to eliminate regions outside of the mandible and to apply different doses to the refined treatment area.

Referring now to FIGS. 4 and 7 at process block 78, the encompassing field 65 is further trimmed, this time manually using the cursor control device 44 to remove the regions outside of the mandibles 66.

At this time, the encompassing field 65 may be partitioned by the drawing of a partition line 73 to create two distinct dose regions 80a near the tumor volume 20 and 80b further removed from the tumor volume 20. Each of these regions may be assigned a different dose. The tumor volume 20 may be individually contoured and given a separate dose definition.

Referring again to FIG. 4 at the final step of process block 82, the refined encompassing field 65, now termed a dose map, may be provided to the treatment planning program 35 of FIG. 3 to generate a treatment plan controlling the intensity of the rays 14 of the beam 12 as shown in FIG. 1 for positions 18a and 18b.

A preliminary analysis of the use of this technique as shown in the following Table 1 indicates that the "subtractive" approach of the present invention is a substantial improvement over conventional non-IMRT treatment and is comparable to "target definition" IMRT which is substantially more time consuming than the present invention.

TABLE 1

| Method | Contoured CTV Volume (CM²) | GTV Dose Volume (CM²) | CTV Dose Volume (CM²) | Spinal Cord Dose (Max) | Parotid Gland Dose (Mean) |
|---|---|---|---|---|---|
| Conventional | N/A | 421 | 838 | 49.1 | 63.1 |
| Target Drawing | 350.2 | 123 | 628 | 40.0 | 21.0 |
| Avoidance Drawing | 579.4 | 138 | 699 | 39.8 | 22.1 |

Figure 8:
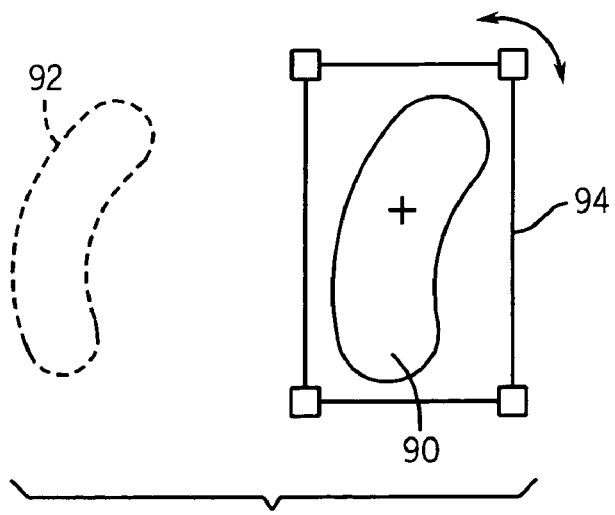
FIG. 8 is a detail of a display on the graphical interface of the computer of FIG. 3 showing application of a standard library area to an image structure.

Referring now to FIG. 8, both the encompassing field 65 and the subset fields 70, 72, 74 may be applied by adapting predefined templates 90 to a particular anatomical area 92. A template 90 may be taken from the template library 50 of FIG. 3 and may represent encompassing areas or subtracting areas that have been predefined for use by physicians, for example, by experienced practitioners looking at particular patients or composites of patients. Each template 90 may have a manipulation bar 94 surrounding it allowing it to be expanded or contracted, rotated or warped so as to best fit the anatomical area 92. This manipulation of the template 90 may be done while the template 90 is superimposed on a CT slice image 46 to greatly simplify this process.

It is specifically intended that the present invention not be limited to the embodiments and illustrations contained herein, but include modified forms of those embodiments including portions of the embodiments and combinations of elements of different embodiments as come within the scope of the following claims.

We claim:
1. A method of radiation planning comprising the steps of:
 (a) obtaining an image of a patient encompassing tumorous and non-tumorous tissue;
 (b) applying an encompassing field to the image having an area covering the tumorous and non-tumorous tissue;
 (c) using a graphical user interface to subtract subset fields corresponding to radiation sensitive non-tumorous tissues from the encompassing field to define a treatment area; and
 (d) inputting the treatment area to a computer program to generate a radiation treatment plan controlling radiation placement and intensity based on at least one prescribed dose to the treatment area,
 wherein the encompassing field is a pattern from a library of encompassing fields for different procedures and wherein the step of applying the encompassing field fits one encompassing field from the library to the patient image based on anatomical image landmarks.
2. The method of claim 1 further including the step of using the graphical user interface to subdivide the treatment area into at least two zones and applying different prescribed doses to the zones.
3. The method of claim 2 further including wherein the zones include one zone near a tumor having a higher prescribed dose and one zone relatively displaced from the tumor having a lower prescribed dose.
4. The method of claim 1 wherein the image is a transverse slice through a head and neck region, and wherein the encompassing field is an exposure area of two counter-directed beams extending along a lateral axis through the head and neck region.
5. The method of claim 1 wherein the image is a medial slice through a head and neck region and wherein the subset fields are selected from the group covering a spinal cord, parotid gland, mandible, and area outside the mandible.
6. The method of claim 1 further including wherein the encompassing field is applied to the image by tracing a periphery of the encompassing field.
7. The method of claim 1 further including wherein the fitting is a translation and rotation of the library encompassing field.
8. The method of claim 1 further including wherein the fitting is a warping of the library encompassing field.
9. The method of claim 1 further including wherein the subset areas are applied to the image by tracing a periphery of the subset fields.
10. The method of claim 1 further including wherein the subset areas are patterns from a library of subset fields for different procedures and wherein the step of subtracting subset fields fits a library subset field to the patient image based on anatomical image landmarks.
11. The method of claim 10 further including wherein the fitting is a translation and rotation of the library subset field.
12. The method of claim 10 further including wherein the fitting is a warping of the library subset field.
13. A radiation planning system comprising an electronic computer and a stored program executing on the electronic computer to:
 (a) display an image of a patient encompassing tumorous and non-tumorous tissue;
 (b) accept first commands from a user to apply an encompassing field to the image having an area covering the tumorous and non-tumorous tissue;
 (c) accept second commands from the user to subtract subset fields corresponding to radiation sensitive non- tumorous tissues from the encompassing field areas to define a treatment area; and (d) output the treatment area for use in generating a radiation treatment plan controlling radiation placement and intensity based on at least one prescribed dose to the treatment area, wherein the first commands from the user are a selection of a library encompassing field from a library of encompassing fields for different procedures and fitting of the library encompassing field to the patient image on anatomical image landmarks in patient image.

14. The apparatus of claim 13 wherein the stored program further accepts third commands from the user to subdivide the treatment area into at least two zones and applying different prescribed doses to the zones.

15. The apparatus of claim 13 further including a cursor control device and wherein the first commands from the user are cursor commands that trace out a periphery of the encompassing field.

16. The apparatus of claim 13 wherein the first commands from the user are translation and rotation commands translating and rotating the encompassing field with respect to the patient image.

17. The apparatus of claim 13 wherein the first commands from the user are image warping commands warping the encompassing field with respect to the patient image.

18. The apparatus of claim 13 further including a cursor control device and wherein the second commands from the user are cursor commands that trace out a periphery of the subset fields.

19. The apparatus of claim 13 further including wherein the subset areas are patterns from a library of subset fields for different procedures and wherein the step of subtracting subset fields fits a library subset field to the patient image based on anatomical image landmarks.

20. The apparatus of claim 19 wherein the second commands from the user are translation and rotation commands translating and rotating the library subset field with respect to the patient image.

21. The apparatus of claim 19 wherein the second commands from the user are image warping commands warping the library subset field with respect to the patient image.

* * * * *

UNITED STATES PATENT AND TRADEMARK OFFICE
CERTIFICATE OF CORRECTION

PATENT NO. : 7,508,967 B2
APPLICATION NO. : 11/110461
DATED : March 24, 2009
INVENTOR(S) : Paul M. Harari et al.

Page 1 of 1

It is certified that error appears in the above-identified patent and that said Letters Patent is hereby corrected as shown below:

In the Specification

Column 1, Lines 14-16:
Delete the phrase:
"This invention was made with United States government support awarded by the following agencies; NIH CA88960. The United States has certain rights in this invention."
And replace with:
--This invention was made with government support under CA088960 awarded by the National Institutes of Health. The government has certain rights in the invention.--.

Signed and Sealed this
Eighth Day of December, 2020

Andrei Iancu
*Director of the United States Patent and Trademark Office*